(12) United States Patent
Deterre (10) Patent No.: US 11,171,163 B2
(45) Date of Patent: Nov. 9, 2021

(54) PHOTOSENSITIVE PIXEL STRUCTURE WITH WRAPPED RESISTOR

(71) Applicant: PIXIUM VISION SA, Paris (FR)

(72) Inventor: Martin Deterre, Paris (FR)

(73) Assignee: PIXIUM VISION SA, Paris (FR)

( * ) Notice: Subject to any disclaimer, the term of this patent is extended or adjusted under 35 U.S.C. 154(b) by 360 days.

(21) Appl. No.: 15/573,705

(22) PCT Filed: May 12, 2016

(86) PCT No.: PCT/EP2016/000776
§ 371 (c)(1),
(2) Date: Nov. 13, 2017

(87) PCT Pub. No.: WO2016/180535
PCT Pub. Date: Nov. 17, 2016

(65) Prior Publication Data
US 2018/0151607 A1    May 31, 2018

(30) Foreign Application Priority Data

May 12, 2015    (EP) .................................... 15001427
Jun. 29, 2015    (EP) .................................... 15001922

(51) Int. Cl.
*A61N 1/05* (2006.01)
*H01L 27/144* (2006.01)
(Continued)

(52) U.S. Cl.
CPC ........ *H01L 27/1446* (2013.01); *A61N 1/0543* (2013.01); *A61N 1/36046* (2013.01); *H01L 28/20* (2013.01); *H01L 31/02019* (2013.01)

(58) Field of Classification Search
USPC .......................................................... 607/54
See application file for complete search history.

(56) References Cited

U.S. PATENT DOCUMENTS 5,753,937 A * 5/1998 Shimomaki ........... G02F 1/1396
257/59
2005/0131490 A1    6/2005 Palanker
(Continued)

FOREIGN PATENT DOCUMENTS

| CN | 1431921 | 7/2003 |
|---|---|---|
| CN | 101317128 | 12/2008 |

(Continued)

OTHER PUBLICATIONS

Lorach Henri et al, "Photovoltaic restoration of sight with high visual acuity", Nature Medicine, Apr. 27, 2015, pp. 476-482, vol. 21, No. 5.
(Continued)

*Primary Examiner* — Nicole F Lavert
(74) *Attorney, Agent, or Firm* — Workman Nydegger (57) ABSTRACT

The present invention relates to a photosensitive pixel structure (10). The pixel structure (10) comprises a substrate (15) and at least one photosensitive diode (12, 12', 12"), a stimulating electrode (14), and a resistor (16). The resistor (16) is electrically connecting the stimulating electrode (14) and a counter electrode (18). Further, the resistor (16) is at least partially covered by the stimulating electrode (14) and/or the resistor (16) is at least partially covered by the counter electrode (18).

27 Claims, 6 Drawing Sheets

(51) Int. Cl.
*A61N 1/36* (2006.01)
*H01L 49/02* (2006.01)
*H01L 31/02* (2006.01)

(56) References Cited

U.S. PATENT DOCUMENTS

| | | |
|---|---|---|
| 2010/0262208 A1 | 10/2010 | Parker |
| 2012/0109292 A1 | 5/2012 | Barbosa |
| 2012/0109296 A1 | 5/2012 | Fan |
| 2012/0153423 A1* | 6/2012 | Lee .................... H01L 27/1446 257/446 |
| 2014/0111088 A1 | 4/2014 | Shim |
| 2017/0070180 A1* | 3/2017 | Mills ....................... H02S 10/10 |
| 2018/0064929 A1 | 3/2018 | Deterre |
| 2018/0182788 A1 | 6/2018 | Deterre |
| 2019/0009075 A1 | 1/2019 | Deterre |
| 2020/0251507 A1 | 8/2020 | Deterre |

FOREIGN PATENT DOCUMENTS

| | | |
|---|---|---|
| CN | 102222450 | 10/2011 |
| CN | 103260560 | 8/2013 |
| CN | 103681701 | 3/2014 |
| EP | 2361440 | 11/2013 |
| JP | S62172765 | 7/1987 |
| JP | 2006-054252 | 2/2006 |
| JP | 2006-517435 | 7/2006 |
| JP | 2012-506623 | 3/2012 |
| JP | 2014503229 | 2/2014 |
| WO | 2004-067088 | 8/2004 |
| WO | 2008-050726 | 5/2008 |
| WO | 2010-048291 | 4/2010 |
| WO | 2012058477 | 5/2012 |
| WO | 2013-142815 | 9/2013 |

OTHER PUBLICATIONS

Wang Lele et al, "Photovoltaic retinal prosthesis: implant fabrication and performance", Journal of Neural Engineering, Jul. 12, 2012, pp. 1-11, vol. 9, No. 4, Institute of Physics Publishing, Bristol, GB.

PCT/EP2016/000776, Aug. 22, 2016, International Search Report / Written Opinion.

Boinagrov et al., "Photovoltaic Pixels for Neural Stimulation: Circuit Models and Performance", IEEE Transactions on biomedical circuits and systems, vol. 10, No. 1, Feb. 2016, pp. 85-97.

Loudin et al., "Photodiode Circuits for Retinal Prostheses", IEEE transactions on biomedical circuits and systems, vol. 5, No. 5, Oct. 2011, pp. 468-480.

Mandel et al., "Cortical responses elicited by photovoltaic sub-retinal prostheses exhibit similarities to visually evoked potentials", Nature Communications, 4:1980, DOI: 10.1038/ncomms2980, pp. 1-9.

International Search Report and Written Opinion for PCT/EP2016/000690 dated Jul. 29, 2016.

International Search Report and Written Opinion for PCT/EP2016/001073 dated Sep. 5, 2016.

International Search Report and Written Opinion for PCT/EP2016/001545 dated Jan. 3, 2017.

* cited by examiner

PHOTOSENSITIVE PIXEL STRUCTURE WITH WRAPPED RESISTOR

The present invention relates to a photosensitive implant with at least one photosensitive pixel structure comprising a resistor.

Implant systems are known, which help to restore at least a fraction of vision to patients who have lost sight, for instance through degenerative diseases such as retinitis pigmentosa. Vision may at least to a certain degree be restored with an implant by exploiting the fact that although parts of the retinal tissue have degenerated most of the retina remains intact and may still be stimulated directly by light dependent electrical stimuli. This electrical stimulation can be provided by means of an implant system. Such a system typically comprises special goggles, which are placed in front of an eye of a patient and an implant, in particular a sub-retinal implant, which comprises a plurality of electrodes.

In the goggles, typically a camera is provided. The camera is adapted to capture a scene in front of the patient. This captured scene may be translated from visual information into a predetermined IR light pulse signal. The implant in such a case is adapted to receive those IR light pulses and, in response, photosensitive areas on the implant are stimulated based on the scene content received by the camera. The implant then converts the received light into electrical current that may stimulate the residual cells in the retina.

For that purpose, the implants comprise one or more pixel arrays, wherein each individual pixel comprises one or more diode areas, a stimulating electrode and, possibly, a counter electrode. The stimulation electrode is typically arranged in the center of the pixel. Trenches are provided between the individual diodes of a pixel and between individual pixels of an array in order to isolate those specific areas from one another. Electrical connections between the diodes and the electrodes are provided to interconnect the components.

If an IR pulse is directed to a pixel or rather to a photosensitive area of a pixel, an electrical pulse is generated by the corresponding photodiode circuit in response thereto.

In order to reliably stimulate residual cells, on the one hand, the current density, i.e., the charge, which is actually delivered per phase per electromagnetic pulse, e.g. per IR pulse, in a predetermined time, should be as high as possible in order to sufficiently stimulate residual cells. On the other hand, the current density should not be too high. Otherwise, tissue damage or damage to the electrode or electrodes may occur. Further, the voltage across the individual electrode should not surpass the hydrolysis limits, since otherwise the surrounding water will dissociate. Again, potential damage to the surrounding tissue as well as electrode degradation may be the consequence thereof. Further, the voltage applied to the electrodes of the implant should ideally fall back to zero volt after a stimulation pulse and prior to any subsequent pulses, to allow positive and negative charges applied by the implant to be balanced. Otherwise, electrodes could deliver some residual DC current which could damage the surrounding tissue as well as the electrode itself. Prior art systems often fail to either provide a high charge or to allow satisfying charge balancing, or both. Further drawbacks of prior art systems may be found in that the electrode size, diode size and resistor resistance may not be adapted freely.

It is further known that electrode arrays comprise electrodes, i.e. at least a stimulating or working electrode, and at least a counter electrode, also referred to as return electrode, with an additional resistor provided in an electrical circuit between the electrodes. This additional resistor also may be referred to as shunt resistor. Wang et al. (Photovoltaic retinal prosthesis: implant fabrication and performance; J Neural Eng. 2012 August; 9(4)) describe that the addition of a shunt resistor will help to speed up the discharge phase of the stimulation wave form. Loudin et al. (IEEE transactions on biomedical circuits and systems; volume 5) suggest the use of a shunt resistor for photodiode circuits in retinal prostheses. Similarly, Mandel et al. (Cortical responses elicited by photovoltaic sub-retinal prostheses exhibit similarities to visually evoke potentials; Nature Communications) and Boinagrov et al. (Photovoltaic Pixels for Neural Stimulation: Circuit Models and Performance; IEEE) refer to optically-activated neurostimulation by means of sub-retinal arrays of photovoltaic pixels. Mathieson et al. (Photovoltaic retinal prosthesis with high pixel density; nature photonics) also describe a retinal prosthesis system with sub-retinal photodiode arrays.

The shunt resistor allows the charge delivered during the first phase of the IR pulse to be rapidly discharged and to control the charge, which is actually delivered to the tissue. If the shunt resistor has a high resistance or if there is no shunt resistor, the charge delivered during the first phase of the pulse may not rapidly discharge. Therefore, the time for the voltage to fall back down to zero increases. Therefore, charges might not be balanced sufficiently quick prior to a further pulse. A high resistance of the shunt resistor therefore could limit the capacitance available for the next pulse and thus the delivered charge in steady state would be reduced.

On the other hand, a low resistance of the shunt resistor would allow the charge to discharge rapidly and fully, but a significant fraction of the photogenerated charge would be lost in the shunt resistor and the charge delivered to the tissue would be reduced.

Therefore, it is important, to ideally adjust the shunt resistor, in particular the resistance of the shunt resistor, to the properties of the electrodes and, in fact, the entire pixel structure, such as the diode size and number.

At the same time, the surface area of the resistor, which inevitably is provided on a surface of the substrate of the pixel structure, competes with the area available for the photosensitive diode or diodes. That is because the resistor, which is provided on the surface of the substrate, has to be electrically isolated from the photo-electrically active areas to ensure correct functioning of the pixel structure. Generally, the resistance of the resistor depends on the size of the resistor, such as its length or its cross section. Design considerations and desired properties of the pixel structures, however, limit the degrees of freedom for the resistor design. In particular, any reduction of the photosensitive area by the resistor is undesired. Otherwise, the efficiency of the pixel structure may be decreased. This would, for instance, be the case, if the mere size of the resistor were increased between the stimulating electrode and the counter electrode, which commonly increases the area covered by the resistor. Thus, the area available as photosensitive area would be reduced by the same extend as the space required for the resistor is increased.

One alternative approach to increasing the resistance of the resistor may be by providing a high-ohmic resistance by only lightly doping a polysilicon stripe, which forms a base layer of the resistor, on the substrate. That approach, however, generally results in an undesirably large variability in the value of the fabricated resistor, if the doping density becomes too low and harder to control. That may possibly render the device useless for the intended application.

One further option to increase the resistance without increasing the surface area may be the reduction of the width of the resistor. However, resistances typically required are in the kOhm- or MOhm-range, such that fabrication limits may be reached for resistors with adequately narrow structures.

It is therefore an object of the present invention to provide a photosensitive pixel structure, which omits at least one of the disadvantages of prior art systems. In particular, the present invention has the objective to allow provision of a well-suited resistor for the specific requirements of various photosensitive structures, while allowing facilitated production.

The problem is solved according to the invention with a pixel structure according to claim 1, a pixel array according to claim 9 as well as an implant according to claim 11. Further, the problem is solved by a method according to claim 13. Advantageous developments are subject to the dependent claims.

According to an aspect of the present invention, a photosensitive pixel structure comprises a substrate and at least one photosensitive diode, a stimulating electrode, and a resistor provided on the substrate. The resistor is electrically connecting the stimulating electrode and a counter electrode. Further, the resistor is at least partially covered by the stimulating electrode. The resistor may in addition or alternatively be partially covered by the counter electrode.

Particularly in cases where a pixel array is provided, one counter electrode may be provided for multiple pixel structures or for all pixel structures on the array. In those cases, the counter electrode may also cover a plurality or all of the resistors connected with the counter electrode, at least partially. It should also be noted that such a counter electrode does not necessarily have to cover all of the resistors connected therewith to the same degree.

By providing the resistor below the stimulating electrode and/or the counter electrode, the resistor may be elongated, and thus its resistance may be increased, without having to either vary the doping density of the resistor or the cross section of the resistor. The surface area available for the photosensitive diodes may therefore remain unaffected. That way, pixel structures with various properties, such as differing electrode sizes, maximized photosensitive areas or decreased pixel size may be generated. A required resistivity of the resistor of the pixel structure may be determined and a particular length of the resistor may easily be implemented into the design of the pixel structure.

In order to isolate the resistor from the respective electrodes, the resistor may be covered by an additional isolating layer, such as an $SiO_2$ or an SiC layer. Accordingly, except for connection points between the resistor and the respective electrode, the isolating layer may be sandwiched between the resistor and the electrode. Further, in order to isolate the resistor from the pixel structure, the resistor may be provided on an isolating layer, such as an $SiO_2$ layer. The isolating layers may also be provided on further parts of the pixel structures, without departing from the scope of the present invention.

In order to determine the length of the resistor, when assuming a predetermined resistivity, width or cross section of the resistor, and its desired resistance, the Eqn. (1) below may be used:

$$R = \rho \cdot L / S \quad \text{(Eqn. 1)},$$

wherein R is the resistance of the resistor, $\rho$ is the resistivity, S is the section area of the resistor, i.e. the product of its width by its thickness for a typical rectangular section resistor, or may be a cross section area of the resistor, and L is the length of the resistor. Accordingly, the desired length L of the resistor for a required resistance R and a specific section area L and resistivity $\rho$ is generally determined according to Eqn. (2):

$$L = (R \cdot S)/\rho \quad \text{(Eqn. 2)}.$$

It will be noted that within technological limits, further parameters such as the section area S, i.e. the width and height of the resistor, and the resistivity $\rho$ may alternatively or additionally be altered, e.g. by varying doping parameters, in order to provide a required or desired resistance according to above cited Eqn. (1).

Those skilled in the art will note that the resistance R, in order to provide a more accurate assessment of the electrical properties of the resistor, may also refer to a material sheet resistance Rsq. That sheet resistance characterizes a material layer, i.e. a material and its thickness in a height direction from a substrate or underlying layer. Typically, using the material resistivity Rho, and the resistor thickness T, the sheet resistance theoretically is Rsq=Rho/T. Departing from the formula defining a resistance of a resistor .R=Rho/(T*W)*L where L is the length and W the width of the resistor, it follows R=Rsq*L/W. The ratio L/W gives a "number of squares" of the resistor for its specific length and resistance.

As the sheet resistance, physically, is a resistance, its unit theoretically is [Ohm]. However, in order to characterize the sheet resistance within the context of the present invention, the unit "Ohm per square" or [Ohm/sq] is used.

To provide an example, a resistor with a length ten times bigger than its width will have a number of squares of 10 squares. If such a resistor comprises a material with an Rsq of 50 kOhm/sq that means that the resistor will have a 500 kOhm resistance. According to the invention, a length of the shunt resistor may be varied, e.g., between 10 and 1000 µm. Preferably, the length of a shunt resistor is between 50-500 µm.

According to the application of the present invention, typically, a high value resistor is desired. That may, on the one hand, be achieved with a high sheet resistance film. This, however, would increase the thickness of the pixel structure. Alternatively, a thin and/or elongated resistor may be provided, i.e., a resistor with a high number of squares.

According to the present invention, the material sheet resistance Rsq shall be in a range from 100 Ohm/sq to 100 kOhm/sq, preferably in the range of 1 kOhm/sq-100 kOhm/sq. Resistors may thus be provided with a total resistance in the kOhm-MOhm range by increasing the length, i.e. increasing the number of squares, of the resistor.

According to advantageous developments of the present invention, the resistor is of an elongate type. "Elongate" in that context shall be understood as an appearance, wherein at least one dimension, preferably the longitudinal dimension defining the length, is significantly bigger than the remaining dimension or dimensions of the elongate structure. For the understanding of the present invention, an elongate resistor is a resistor which, in a longitudinal direction of the resistor, is by far bigger, i.e. longer, than in any transversal direction determining either the thickness or the width or cross section of the resistor. According to the above definition, an elongate resistor accordingly has a high number of squares. A resistor according to some embodiments of the present invention may be provided in a straight shape or at least partially in a straight shape. It will, however, be noted that an elongate resistor is not restricted to a straight shape but may have a variety of shapes.

Accordingly, in some embodiments of the present invention, the resistor is provided with a wrapped shape, in particular in an area where it is covered by the stimulating electrode and/or in an area where it is covered by the counter electrode. In context with the present invention, such a "wrapped shape" shall include a coiled shape, a spiral shape, a hexagonal shape, angled shape or any other kind of shape which is deemed suitable and which may be achieved by those methods commonly used to form a resistor structure on a substrate. Many alternative ways to arrange the resistor may also be chosen, such as a zig-zag-pattern or a meandering pattern, which are deemed to be described by the term "wrapped" in the context of the present invention, without departing from the scope of the present invention.

In order to provide the resistor with such an individually adapted length and shape, a highly resistive material with controlled or controllable resistivity is provided as a resistor base layer on the substrate. That material shall further allow thin film deposition in semiconductor-compatible processes. Such a material may, for instance, be silicon. The deposited resistor base layer may then be doped in order to set or control the resistivity of the final structure. When using silicon, or another material, doping may, for instance, be conducted with boron, arsenic, phosphorous, antimony, aluminium, indium or gallium. The silicon may be deposited in an amorphous or polycrystalline form. Other materials besides silicon may also be used to form the resistor. However, advantageously, these materials should be compatible with semiconductor fabrication processes, should be patternable and should bring along the required resistivity.

In particular embodiments, the resistor may have a wrapped shape in an area where it is covered by the stimulating electrode and/or the counter electrode. The resistor may further have a straight shape in an area, which is not covered by either one of the stimulating electrode or the counter electrode, e.g., in an area on the surface of the substrate, which is shared with the photosensitive diode area of the pixel structure. The resistor according to the present invention, however may also have a straight shape in an area covered by, e.g. the stimulating electrode. It will be noted that the length of the resistor, even with a straight shape, may still be varied without altering the shape of the resistor, by changing the position of an electrical connection between the resistor and the stimulating electrode.

Providing the resistor with a wrapped shape allows to increase the length of the resistor in a longitudinal direction of the resistor. That way, a resistor with predetermined cross section area or width and with sufficient doping rates to sufficiently and reliably define the electrical properties of the resistor may be provided with a sufficiently high resistance. Therefore, by covering the resistor at least partially and by wrapping the resistor in those covered areas, even for small pixel structures, high-ohmic resistors may be provided without using up additional surface area for photoelectrical conversion on the surface of the substrate.

In some embodiments of the present invention, the substrate of the photosensitive pixel structure is a silicon substrate, preferably a monocrystal line silicon substrate, which may also be referred to as a device layer. The substrate may in particular be of a so-called silicon on insulator type, and comprise at least a layer of $SiO_2$. The $SiO_2$ layer may be provided on a surface of the substrate, on which the photosensitive diode area and/or the stimulating electrode is provided. Further, the resistor may be provided on that $SiO_2$ layer. Alternatively or in addition, the $SiO_2$ layer may be provided on a surface opposing the surface comprising the photosensitive structure and/or along the walls of trenches in the substrate. The $SiO_2$ layer may also be provided around the entire pixel. Provision of a silicon substrate may allow improved electrical properties. Further, providing a $SiO_2$ layer may enhance the electrical properties at the interface of the silicon layer and the $SiO_2$ layer, thereby increasing the performance of the pixel structure. Apart therefrom, providing a $SiO_2$ layer may allow improved doping results with the resistor material thereon. The $SiO_2$ layer may be provided on the substrate by thermal oxidation. That way, insulator layers, also along trenches between diodes or pixel structures through the respective layers, may be provided. Alternatively, the $SiO_2$ layer may also be provided by deposition methods such as low pressure chemical vapor deposition (LPCVD).

As an alternative for a substrate material, germanium may also be used instead of silicon in some embodiments of the present invention.

According to a further development of the present invention, the counter electrode is arranged around the stimulating electrode. In addition or alternatively, the counter electrode may be arranged around the at least one diode. Likewise, the resistor may be arranged around the stimulating electrode and/or arranged around the at least one diode.

The term "arranged around" in the context of the present invention shall be understood such that the counter electrode and/or the resistor have an elongate extension and, in that elongate extension, extend, at least partially, around an area on the substrate of the photosensitive pixel. That area may be defined by the stimulating electrode and/or by the at least one or more diodes. In the case that a plurality of diodes is provided, the counter electrode may be arranged around one or all of the diodes. According to that definition, the counter electrode and/or the resistor does not necessarily have to be directly adjacent to the, e.g., stimulating electrode. There may, in particular, be a photosensitive area between the stimulating electrode and the counter electrode and/or the portion of the resistor being arranged around the stimulating electrode.

With such an arrangement, an improved light detection and stimulation process may be established with enhanced homogeneity of the field distribution of the electric field, which is created by the stimulating electrode. Preferably, the counter electrode is arranged symmetrically, such as circularly or hexagonally or similar, around the stimulating electrode. It will be understood by those skilled in the art that the resistor in these embodiments will electrically connect the stimulating electrode and the counter electrode by traversing the diode area, even if only one diode is used, rendering a part of the surface area of the substrate unusable or blind for light reception.

The resistor may extend in parallel to the counter electrode in an area of the pixel structure covered by the counter electrode. That means, the resistor may be provided such that it has the same or similar contour and shape as the counter electrode. Thereby, the resistor may extend along a predetermined length of the counter electrode around the pixel structure. As the area covered by the counter electrode may not be used for light reception of the pixel structure, anyway, the length of the resistor in an area covered by the counter electrode may thus be elongated at least by the length of the lateral extension of the counter electrode, without using up additional space required as diode area of the pixel structures. The size of the pixel structure may thus be reduced. In a pixel array, this may eventually allow a higher resolution of the array as a whole.

The resistor, according to some embodiments of the present invention, may have a width in a lateral direction, i.e.

in a direction transversal to its elongated extension of up to 10 μm, preferably below 5 μm. Most preferably, the width of the resistor is below 2 μm. Such a width may well be generated by common fabrication methods, while such widths still allow to reduce the space used of the potentially light sensitive area of the pixel structure's surface. As with decreased width, the control of resistance strongly varies and depends on the accuracy of the doping process and other parameters, preferably, the width of the resistor is more than 100 nm. Preferably, the width of the resistor is more than 500 nm. Accordingly, the resistor has a preferred range of between 500 nm and 2 μm.

In a photosensitive pixel structure, the thickness of the resistor on the substrate or underlying layer desirably is as thin as possible. According to some embodiments, that thickness of the resistor is about 1 μm or below. Preferably, the thickness of the resistor is about 500 nm or below. Further, as set out above, to enable for a sufficient amount of control, the resistor may not be too thin. Accordingly, the resistor has a thickness of more than 50 nm, preferably more than 100 nm. Accordingly, the resistor may have a thickness in the range of about 50 nm to 1 μm, preferably of the range 100 nm-500 nm.

The doping of the resistor, i.e. the implant dose, may be between $10^{12}$-$10^{16}$ atoms/cm$^2$. Structures with such thicknesses and doping densities may be produced by common methods. Therefore, according to the invention, a production of a pixel structure with sufficiently high resistance values of its shunt resistor may be facilitated.

The resistor on the substrate or any layer provided on the substrate may for instance have an amorphous or a polycrystalline structure.

In a further development of the present invention, in one pixel, a plurality of diodes, such as two diodes or three diodes, are provided.

According to another aspect of the present invention, a pixel array is provided wherein the pixel array comprises at least one, preferably a plurality of photosensitive pixel structures according to the first aspect of the present invention, wherein the pixel structures are arranged in an array.

In particular, the pixel structures may be arranged such that the space available on the substrate for the pixel array is optimally used. This may for instance be achieved by providing the individual pixel structures in a hexagonal shape such that one pixel is adjacent to six further surrounding pixels. That way, the pixel array may be provided with increased resolution. However, the individual pixel structure may also have an octagonal or rectangular shape. The pixel structure may also have circular or diamond shape or any other, even arbitrary shape, without departing from the scope of protection of the present invention. It will be understood that the pixel structures within an array may also have different shapes, e.g., a fraction of the pixel structures may have a hexagonal shape, while others may for instance have a pentagonal shape. This may allow to provide or improve an array with a curved shape or with flexible characteristics.

In such a pixel array, a central counter electrode may be provided, which is connected to a plurality of stimulating electrodes. The connection of the respective stimulating electrodes with the central counter electrode may each be provided by means of a resistor. One or more resistors, in such a case, may be arranged below the counter electrode, i.e., the counter electrode may cover one or more of the resistors, in particular one or more of the resistors connected with the counter electrode.

The individual pixel structures of a pixel array may all be sensitive for the same stimulation wavelength of incident light. The pixel array may, however, also be adapted to comprise pixel structures or groups of pixel structures which are sensitive for other wavelengths of incident light. In order to enable for such measures, a portion of the photosensitive pixel structures may be adapted to a specific wavelength. According to the present invention, this may in particular be enabled by altering the properties of the light sensitive areas, i.e. diodes, electrodes and respective electrical connections, such as the resistor. In order to adapt the resistance of the resistor to the individual properties of a pixel structure of a pixel array, during production, resistors may be provided with the same width and the same dope-atom density, but with altered length of the respective resistors. That way, also the production of pixel structures with varying electrical properties within the same pixel array, such as post-pulse relaxation or charge balancing characteristics, can be facilitated.

According to a further aspect of the present invention, an implant is provided, which comprises a photosensitive pixel array or at least one photosensitive pixel structure. By providing a photosensitive pixel array or structure to the implant, the implant is rendered a photosensitive implant, which may provide electrical stimulation or energy supply when implanted. In particular, the photosensitive implant may provide electrical stimulation to living tissue, such as neural tissue, or cells. In particular, the implant may allow electrical stimulation to retinal tissue of an eye of a subject. That way, it may be enabled to at least partially restore vision to a patient.

In order to stimulate living tissue or cells, the implant is implanted into a tissue of, e.g., a patient or an animal. When implanting, the electrodes preferably are arranged such that they may get into contact or at least are in functional proximity with the tissue or the cells to be stimulated.

It will be understood that the photosensitive structure, the photosensitive pixel array and/or the implant according to one of the aspects of the present invention may stimulate a variety of living tissues or cells. In particular, the devices according to any of the aspects of the present invention may be used in connection with neural tissue of the eye, in particular the retina, neural tissue of the ear, in particular the inner ear, tissue, in particular neural or muscular tissue, of the heart, spine, muscles or various organs of a body. Apart therefrom, the devices according to any of the aspects may be used to stimulate nerves or nerve cords directly or indirectly, e.g., by unspecific stimulation of tissue areas proximate to a nerve or nerve cord.

According to the invention, an electrical charge is generated by a pixel according to the present invention on a stimulating electrode upon detection of a sufficient light stimulus by the photoactive pixel area, i.e., on the diode or diodes of the pixel structure. Thus, any position within a tissue may be suitable to receive the implant, provided a light excitation of at least one diode, and thus the generation of a charge on the stimulating electrode connected with that diode, may be realized.

Such excitation by light through the diode on a pixel may be applied by an external light source, i.e. a light source external to the body, in which the implant is provided. Alternatively, a light source may be provided by a further implant or through further means, from within the body, in which the implant is provided. In particular, infrared light or light pulses may be used to illuminate the photosensitive area of a pixel. Such IR light may also be adapted to penetrate through several layers of tissue, in particular a skin of a patient carrying the implant or further tissue layers, e.g. from outside of an organ or living tissue to be stimulated.

In a preferred embodiment, the implant is a sub-retinal implant. That allows to implant the implant within the eye of a patient, i.e. subretinally, in order to bypass any damaged tissue of the retina. Consequently, the electrical impulses may be generated in close proximity to the sensitive neural cells which are still functional in the retina. Advantageously, the photosensitive implant may also comprise a sealing layer or a sealing coating, in order to protect the implant structure from either of corrosion or damage.

According to yet another aspect of the present invention, a method to provide a pixel structure, and, eventually, a pixel array or an implant according to one of the aspects of the present invention comprises as a first step the provision of a substrate. On the substrate, in a further step, at least one photosensitive diode area is provided. Further, a resistor is provided on or within the substrate in a region, which is not occupied or not intended to be occupied by the at least one diode. In addition, a stimulating electrode and/or a counter electrode are provided on the substrate. The stimulating electrode and/or the counter electrode are provided such that they cover the resistor at least partially.

In some embodiments of the method according to the present invention, the resistor is provided as a straight, elongate structure. In addition or alternatively, the resistor may at least partially be provided in a wrapped shape. In particular, the resistor may be provide in a wrapped shape, preferably in a spiral or coil shape, particularly in an area, which, in subsequent steps, will be covered by the stimulating electrode.

It is to be noted that the order of the steps to provide a pixel structure, device or implant according to the invention, may be applied in a different order than listed herein.

In some embodiments, the resistor is provided by atom doping of the substrate or of an additional substrate structure, such as an amorphous or polycrystalline structure, in particular silicon. This may allow production of small structures with highly definable electrical properties.

In a further preferred embodiment the resistor is provided by atom doping of a thin strip of a material selected from the group comprising amorphous silicon and polysilicon, such that the resistor can be provided in an efficient way.

The resistor may be provided by forming a first shunt resistor of a first material and at least a second shunt resistor of a second material different from the first material and connecting the first and the at least on second shunt resistor in series. This method gives way for a better fine tuning of the shunt resistor value.

Alternatively, the resistor may be provided by forming a first shunt resistor of a first material and at least a second shunt resistor of a second material different from the first material and connecting the first and the at least one second shunt resistor in parallel. This method gives way for a better fine tuning of the shunt resistor value.

In an advantageous embodiment, at least the first material is a metal, especially a metal forming a metallization layer that interconnects the photosensitive diodes to each other and which interconnects the photosensitive diodes to the electrodes. With this embodiment, a further efficient method of providing a shunt resistor is realized that may use existing metallization layers.

It is further possible to provide the entire pixel array for the implant or one or more of the pixel structures within the pixel array with a diode, which is receptive for a particular wavelength, while other pixel structures may be desired to be receptive for another wavelength. Properties of the diodes may be adjusted by differently manipulating, e.g., doping, the substrate, in order to provide the photosensitive diode area.

According to the invention, for each pixel structure, different resistance of its shunt resistor may be provided by altering the length of the resistor, with all remaining parameters, such as resistivity, cross section, height and so forth being constant on one substrate. That way, pixel structures with different electrical properties within a pixel array may be generated.

Consequently, the performance and the functionality of the pixel array may be enhanced and configured to multiple purposes. In particular, different wavelength signals may be provided for different stimulation schemes, or stimulation of different cells at different electrodes may be allowed. Further, by means of different wavelengths, transmission of information to an implanted control unit of an implant may be enabled, while, at the same time, signal or light transmission for stimulation of cells can be proceeded uninterrupted.

Further details, preferred embodiments and advantages of the present invention will be found in the following description with reference to the drawings, in which.

Figure 1:
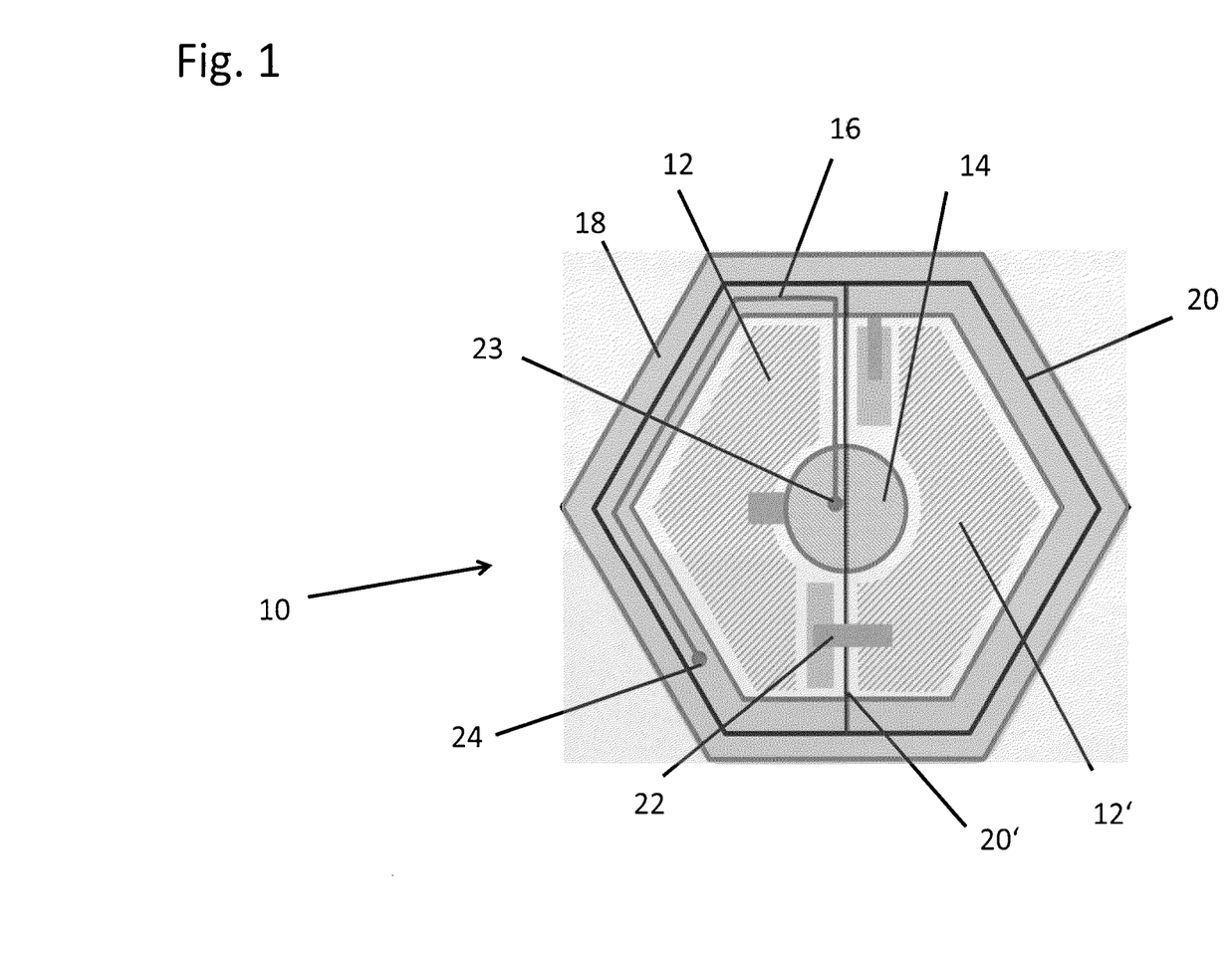
FIG. 1 is an example of a photosensitive pixel structure with a resistor according to an embodiment of the present invention.

FIG. 1 shows a photosensitive pixel structure 10 according to an embodiment of the present invention. The photosensitive pixel structure 10, in the following also referred to as a pixel, comprises a photosensitive diode 12, a central electrode 14 and a resistor 16. At an outer periphery of the pixel structure 10, a counter electrode 18 is provided, which is also often referred to as return electrode. The counter electrode 18 can be placed on each individual pixel structure 10, for instance at the periphery of each pixel structure 10, as shown in FIG. 1. That means, the return electrode is local and in-between the different central electrodes of an array 1 of pixel structures as will be discussed in context with FIG. 3. This is typically also referred to as a "bipolar" configuration.

For such a bipolar arrangement, two configurations are possible. The return electrodes may be disconnected from one another. That means, pixels in that case are completely independent from one another. Alternatively, all or groups of return electrodes of individual pixel structures or groups of pixel structures may be connected together, in order to effectively creating a sort of grid-like structure. Such a structure may, for instance, comprise a plurality of hexagonal pixels, which may extend over a whole pixel array 1. Examples for such a pixel array are displayed in FIG. 3.

As a further alternative, a central return electrode (not shown) may be placed separate from the pixel structure 10, for instance at a position on a pixel array remote from the pixel structure. Such a central return electrode may in particular be provided at a remote location on the implant. Such a configuration may also be referred to as a monopolar configuration. It is to be noted that the return electrode does not necessarily have to be in a geometrical centre of the implant. Further, it is possible that a plurality of such central return electrodes are distributed over the implant or the pixel array.

Figure 3:
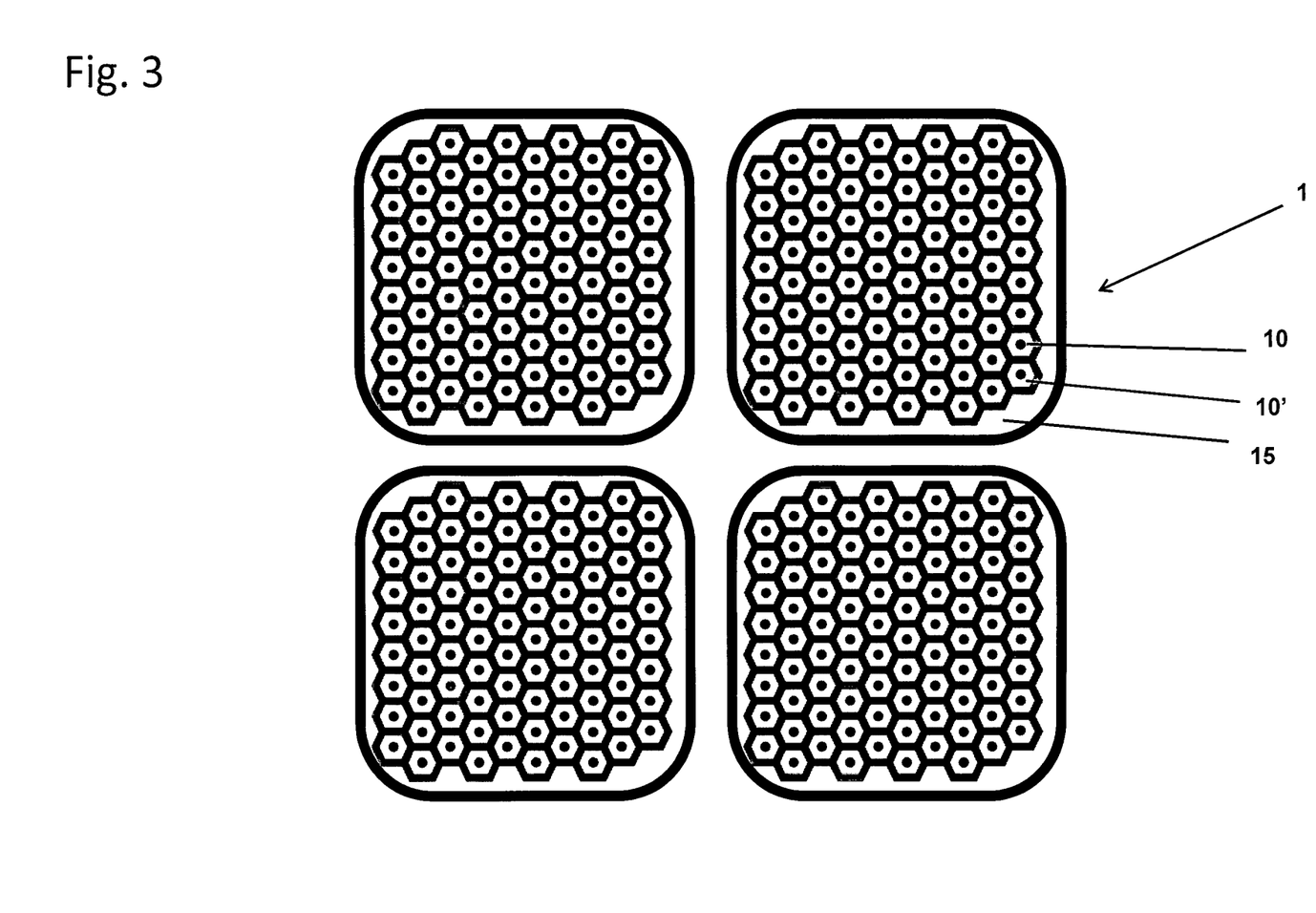
FIG. 3 displays an electrode array according to an embodiment of the present invention.

The pixel structure 10 in the embodiment of FIG. 1 has a generally symmetric hexagonal shape. That hexagonal shape of the pixel structure 10 is defined by trenches 20 arranged around the pixel structure and electrically isolating the pixel structure from adjacent structures. Electrical isolation of the trenches may be ensured by providing an $SiO_2$ layer by deposition or by thermal growing on at least one side wall of a trench 20. Alternatively or in addition, the trenches 20 may for instance comprise or consist of Poly-Silicon. Adjacent to each of the sides of that hexagon, further pixels 10' may be provided. An example for one embodiment of a pixel array 1 of pixels 10, also referred to as an electrode array in the context of the present invention, is shown in FIG. 3. In alternative embodiments, the shape of the individual pixels may also differ. For example, the pixels may have an octagonal or rectangular shape. The pixels may also have circular or diamond shape or any other, even arbitrary, shape, without departing from the scope of protection of the present invention.

Individual pixels are separated from each other by means of the trenches 20. The trench 20 comprises an electrically isolating material. Individual, adjacent pixels 10 preferably are electrically isolated from one another. The counter electrode 18 as shown in the embodiment of FIG. 1 is arranged along the extension of the trench 20 surrounding the periphery of active area of the pixel 10 thus with the same, here hexagonal, contour.

In the embodiment shown in FIG. 1, the pixel 10 further comprises two diodes 12, 12'. The diodes 12, 12' are arranged inscribed within the area of the hexagonal pixel shape. Preferably, the diodes 12, 12' are symmetrically arranged. Between the diodes 12, 12', an isolating trench 20' is provided. The isolating trench 20' between the diodes 12, 12' has generally the same properties as the isolating trench 20. The different diodes 12, 12' of the pixel 10 are therefore basically electrically isolated from one another. It is to be understood that despite trenches 20' arranged within the pixel, i.e. in a substrate 15 of the photosensitive element, electrical contact between objects separated and isolated by trenches 20, 20' may still be established. In the embodiment according to FIG. 1, for instance, the diodes 12, 12' are connected by an electrical contact 22. As will be further detailed with respect to FIG. 4, the diodes 12, 12', that way, are serially connected with respect to one another in the embodiment according to FIG. 1.

The diodes 12, 12' represent, in the projection view of the embodiment according to FIG. 1, a photosensitive area of the pixel 10. In that embodiment, the surface area, i.e. the photosensitive area, of the diodes 12, 12' is essentially symmetric around a symmetry axis of the pixel 10. In the embodiment of FIG. 1 such a symmetry axis may for instance coincide with the trench 20' separating the diodes 12, 12' of the pixel 10. In other embodiments, the number of diodes may be different. In particular, there may be only one diode 12 provided.

That would allow to increase the photosensitive area of the pixel, as no trenches 20' had to be provided to separate individual diodes within the pixel 10. In further embodiments, three diodes 12, 12', 12" or more than three diodes may be provided in one pixel. If more than two diodes are provided in a pixel 10, the individual diodes 12, 12', 12" may also be serially connected with one another, as already discussed for a two-diode pixel structure above.

Diodes within one pixel as well as diodes between different pixels may all be separated by trenches 20, 20' as described above. That may reduce cross talk between diodes and pixels, and thus increase the reliability and resolution of an entire pixel array.

A plurality of diodes, for instance two or three diodes, for one pixel may be provided, if the voltage, as response to a light signal received, needs to be increased. The diodes may for such cases be serially connected, wherein the voltage of a number N of diodes is the factor N higher than the voltage created by one diode only. On the other hand, an increased number of diodes means that fewer light may be collected by each diode, per pixel. The electrical current created by each of those diodes connected in series may therefore be significantly lower when having a plurality of diodes compared to having only one or a few diodes. Typically, the current in a circuit with N diodes is N times less than the current in a circuit with one diode. It is therefore a matter of choice, which of the parameters, i.e., current or voltage, is more desirable for an individual application. In the specific case of neural stimulation, the required stimulation parameters may depend on the tissue and/or the individual cells, in particular neural cells, to be excited, the position of an implant and even individual specifics of a patient, possibly age, state of disease and general physiological condition.

Figure 2:
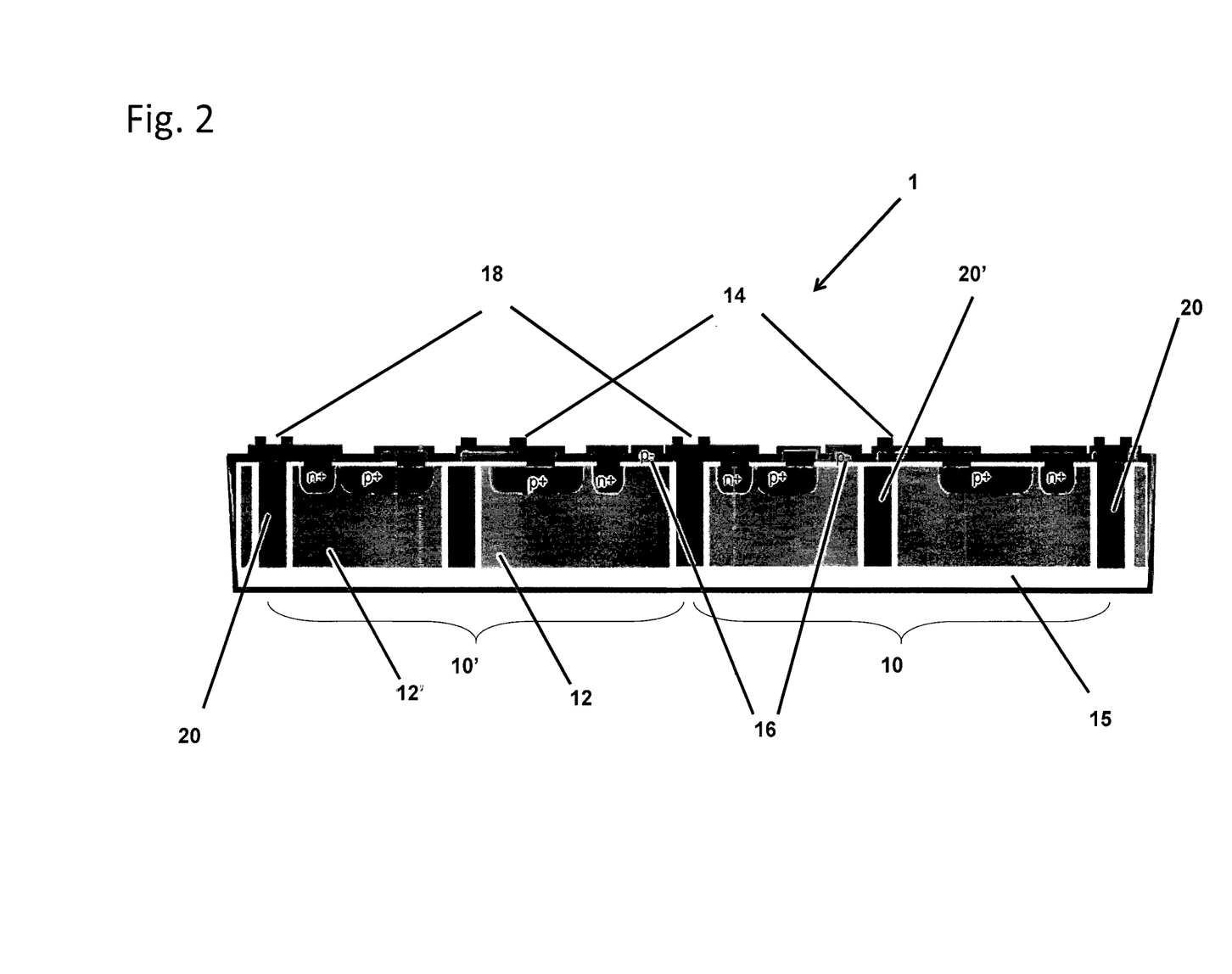
FIG. 2 is a schematic cross-sectional view of a semiconductor structure with two adjacent pixels according to an embodiment of the invention.

Diodes may be provided on the substrate 15 by doping specific areas of the surface of that substrate in a predetermined way, such as by p+ doping one area and n+ doping another, adjacent area, as exemplified in FIG. 2. Accordingly, the area on the substrate surface available for doping is the area, which may then allow light detection. Therefore, the area occupied by the resistor 16 and the trench 20' may not be doped and therefore is lost as photosensitive area. Those skilled in the art will be aware that the doping of the diode may be applied different from the example of FIG. 2, according to the requirements of the application such as wavelength, sensitivity, materials used and others.

As may be further seen in FIG. 1, in the centre of the pixel structure 10, an electrode 14 is provided. Due to its central position, that electrode 14 is also referred to as central electrode. Further, as that electrode typically is used for stimulation, that electrode is also referred to as stimulating electrode. The stimulating electrode 14 in the shown embodiment is provided having a circular shape. The electrode may also have different shapes, such as a shape similar to the shape of the return electrode 18 or the trench 20 reflecting the contour of the pixel 10.

The circular shape of the presently shown embodiment was chosen such that the electrical field from the stimulating electrode 14 may be homogenous. Depending on the intended application, the shape may also include such shapes which allow less homogenous, locally enhanced field distributions.

According to some embodiments of the present invention, the electrode 14 of the pixel 10 shall be adapted for stimulation of surrounding tissue, preferably neural tissue, in particular neural tissue of a retina in vivo. Typically, the electrode comprises platinum, iridium oxide and/or titanium nitride. Alternatively, iridium, platinum iridium, doped diamond or diamond-like carbon or PEDOT:PSS, or other known materials may be used as electrode material. The preferred structure of the electrode material may in particular be a highly porous structure, such as a porous or fractal TiN, a platinum structure or SIROF. Such structures are known and found to be described to be, e.g., "black platinum" or "porous platinum". The thickness of the electrodes may vary from about 100 nm to 3 µm. It is, however, also possible to have an electrode thickness up to or above 10 µm as well, or below 100 nm.

In the embodiment as shown in FIG. 1, the return electrode 18 is provided as an elongate electrode surrounding the pixel and following the contour of the pixels periphery, i.e., in the shown embodiment, the run of the trench 20. In alternative embodiments, the return electrode may also comprise a plurality of electrodes, which are distributed around the pixel structure 10 and around the stimulating electrode 14 in regular or arbitrary distribution. This may in particular be exerted at a peripheral portion of an electrode array 1.

Further, between the stimulating electrode 14 and the counter electrode 18, the resistor 16, also referred to as a shunt resistor, is arranged. That resistor 16 according to the embodiment shown in FIG. 1 of the present invention, is electrically connected to the stimulating electrode 14 and to the counter electrode 18. A connection is established by arranging the resistor 16 on the surface of the substrate proximate to or on the trench 20' between the two diodes 12, 12', as shown in the embodiment of FIG. 1.

Further referring to FIG. 1, the resistor 16 is connected with the circular stimulating electrode 14. In order to connect the resistor 16 with the stimulating electrode 14, a first electrical connection 23 is provided at a first end of the resistor proximate to the centre of the stimulating electrode 14. The resistor extends radially from the point of connection, straight toward the counter electrode 18. Thus, in the embodiment of FIG. 1, the resistor 16 is provided in a straight way in an area covered by the stimulating area and in an area on the surface of the substrate, which is not covered by either the counter electrode 18 or the stimulating electrode 14. At the periphery of the pixel structure 10, below the counter electrode 18, the resistor 16 is shaped to follow the hexagonal shape of the counter electrode 18 forming the outer contour of the pixel structure 10. That means, the resistor 16 here has an angled shape to follow the run of the extension of the counter electrode 18.

In the embodiment of FIG. 1, the length of the resistor extending below the counter electrode 18 is about one sixth of the entire length of the counter electrode 18. However, the length of the portion of the resistor covered by the counter electrode may be longer or shorter when compared to the embodiment if FIG. 1. In particular, the portion of the resistor covered by the counter electrode may have an arbitrary length up to or even above the entire length of the counter electrode 18, i.e. the length of the circumference of the pixel structure 10.

The resistor 16 may be provided by atom doping of a thin strip of a material like e.g. amorphous silicon or polysilicon. Alternatively to what is shown in FIG. 1, the resistor may be a heterogeneous resistor or shunt resistor which comprises a first shunt resistor of a first material and at least a second shunt resistor of a second material different from the first material which are connected to each other in series or in parallel. The first material may be a metal, e.g. a metal forming a metallization layer that interconnects the photosensitive diodes to each other and which interconnects the photosensitive diodes to the electrodes.

In the embodiment shown in FIG. 1, thus, the counter electrode 18 is arranged around the entire area covered by the diodes 12, 12' and the stimulating electrode 14. The counter electrode 18, therein, is separated from the stimulating electrode 14 by that surface area of the substrate 15 implemented as photosensitive diode area. Similarly, the portion of the resistor 16, which is covered by the counter electrode 18 is arranged around the pixel structure 10. However, the resistor in that embodiment of FIG. 1 is only partially arranged around the pixel structure. Examples for embodiments of the present invention, wherein the resistor is arranged essentially entirely around the pixel structure may be found in FIGS. 5 and 6 as described below.

The resistor 16, at a second end of the resistor 16, is connected with the counter electrode 18 by means of a second electrical connection 24. It will be noted that the length of the resistor 16, e.g., to determine or define the resistance of the resistor 16, is the distance between the first electrical connection 23 and the second electrical connection 24 along the direction of extension of the resistor 16. As a common rule, the resistance if the resistor 16 increases with the length of the resistor 16, as defined by Eqn. (1) above.

FIG. 2 shows a sectional side view of a portion of an electrode array 1, showing two adjacent pixels 10, 10'. The pixels 10, 10' correspond to the pixel according to the embodiment as shown in FIG. 1, having two diodes 12, 12'. The same layer structure as shown in FIG. 1 for a two-diode pixel may essentially also be provided for a one-diode or three-diode pixel, analogously. The resistor 16 herein is provided on a surface of the pixel structure 10. According to some embodiments of the invention, the resistor 16 is a conductor, such as a metal structure or wire on the surface of the pixel 10. In some embodiments, the resistor may be made of or comprise silicon. The silicon may be doped silicon. In particular, the silicon may be lightly doped. It is to be noted that the resistor may display various kinds of doping. In the embodiment as displayed in FIG. 2, the resistor 16 is p– doped. However, p+ doping, n– doping or n+ doping may be applied as well depending on the embodiment, as well as further doping methods, materials or mixtures thereof. The same is true for the doping of the diodes 12, 12' 12". The pixel array 1 is provided on the substrate 15, which may be seen in FIG. 3. The position of the resistor on the substrate 15 according to an embodiment of the invention is also displayed in the cross-section view of FIG. 2 in more detail. As may be seen in FIG. 2, the resistor 16 has, in the shown embodiment, a lateral offset from the trench 20'

FIG. 3 shows an array of pixels 10, i.e., a pixel array 1. Since the pixel array 1 is an array of pixels 10, which comprises stimulating electrodes 14 configured to stimulate cells or living tissue, the pixel array may also be referred to as an electrode array. The size of the individual pixel structures 10 in the electrode array 1 may differ and can thus be tuned to different applications. In the array 1 displayed in FIG. 3, the individual pixels 10, 10' are hexagonally formed, which allows a space efficient distribution on the substrate 15. That way, the space available for light sensitive regions on the substrate 15 and within an array 1 may be increased and ideally maximized.

Figure 4:
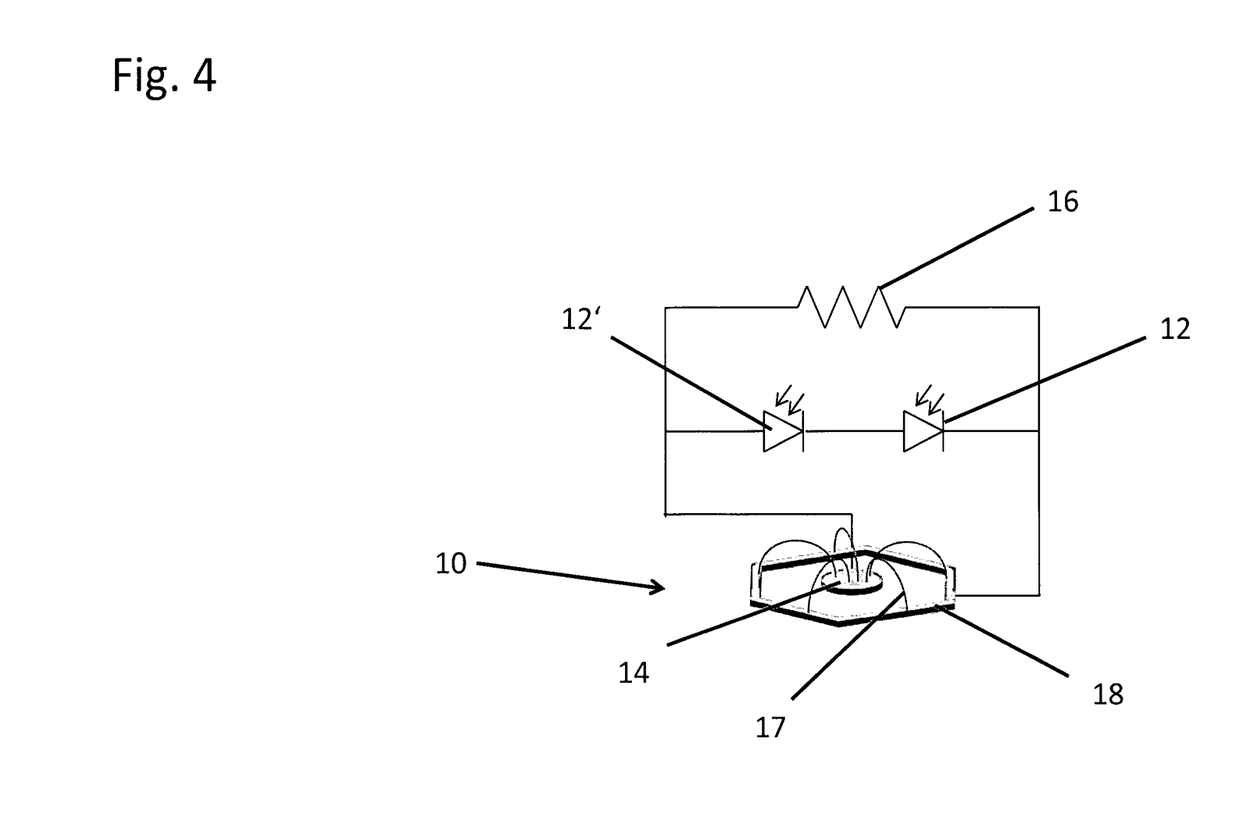
FIG. 4 is a perspective view of the photosensitive pixel of FIG. 1 with a schematic drawing of a wiring circuit.

FIG. 4 shows a schematic perspective view of a pixel 10 according to an embodiment of the present invention. The pixel 10 as shown exhibits the return electrode 20 as a hexagonal elongate electrode. The stimulating electrode 14 here is a circular electrode. If electrical voltage is applied, i.e., when the stimulating electrode 14 generates an electrical pulse in response to incident light, an electrical field, represented by electrical field lines 17 in FIG. 4, is generated. Cells within the proximity of this field may eventually be stimulated, depending on the specifics of the stimulation pulse such as pulse shape, strength, duration, polarity, and so forth. The electrode 14 or electrode array 1 may also be placed in tissue in a way that the tissue, i.e. the cells within the tissue, may directly contact the stimulating electrode 14 and/or counter electrode 18.

The schematic pixel structure 10 of FIG. 4 is provided with two diodes 12, 12', which are serially connected, as shown by the schematic drawing of FIG. 4. The resistor 16, i.e. the shunt resistor, is connected in parallel to the diodes 12, 12'. That way, an electrical circuit with reliable charge balancing and stimulation parameters may be established.

Figure 5:
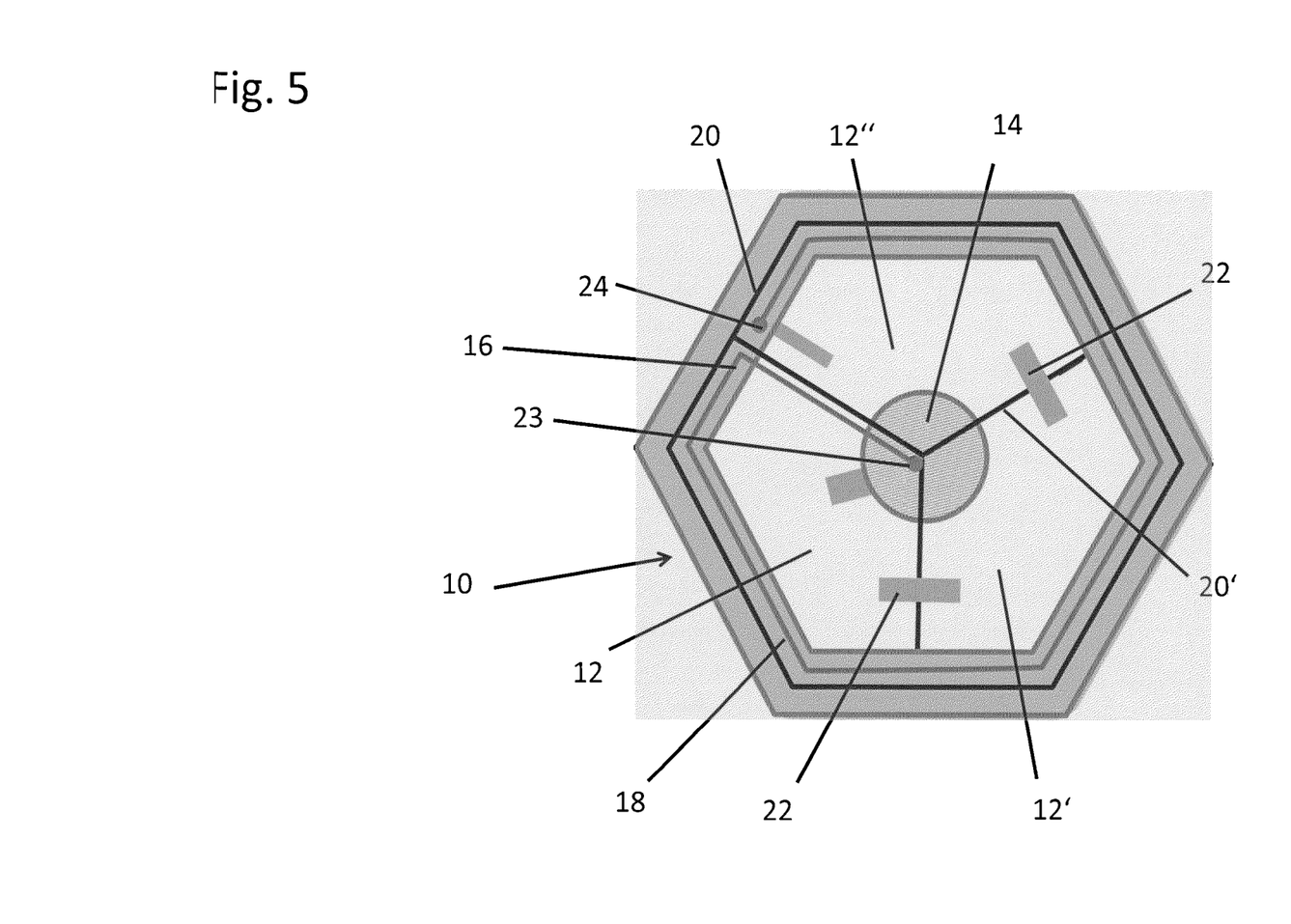
FIG. 5 is an example of a photosensitive pixel structure with a resistor according to an embodiment of the present invention.

FIG. 5 shows an embodiment of the present invention similar to the embodiment as shown in FIG. 1. Same reference signs refer to same or similar components and repeated description thereof is omitted. The embodiment of FIG. 5 differs from the one of FIG. 2 in that a third diode 12" is provided in addition to the two diodes 12, 12', and in that the length of the resistor 16 is longer, i.e. the resistor 16 extends below the counter electrode 18 almost entirely around the pixel structure 10. FIG. 5 thus exemplifies one way according to the invention to increase the length of the resistor 16, and thus its resistance. In different embodiments, the resistor 16 might be shorter, e.g. have a length which only partially extends around the photosensitive area or areas of the pixel structure 10. Further, the number of diodes may be lower or higher than three. In particular, one diode or two diodes may also be provided in further embodiments with a resistor 16 according to the embodiment of FIG. 5. The resistance of the resistor 16 and thus its length, may depend on the size of the photosensitive area, i.e., the size or area of the diode 12, 12', 12", and/or on the size or area of the stimulating electrode 14 provided on the pixel structure 10.

In the embodiment of FIG. 5, the three diodes 12, 12', 12" are serially connected by means of the electrical connections 22. Alternative configurations may be possible, as already indicated above.

Figure 6:
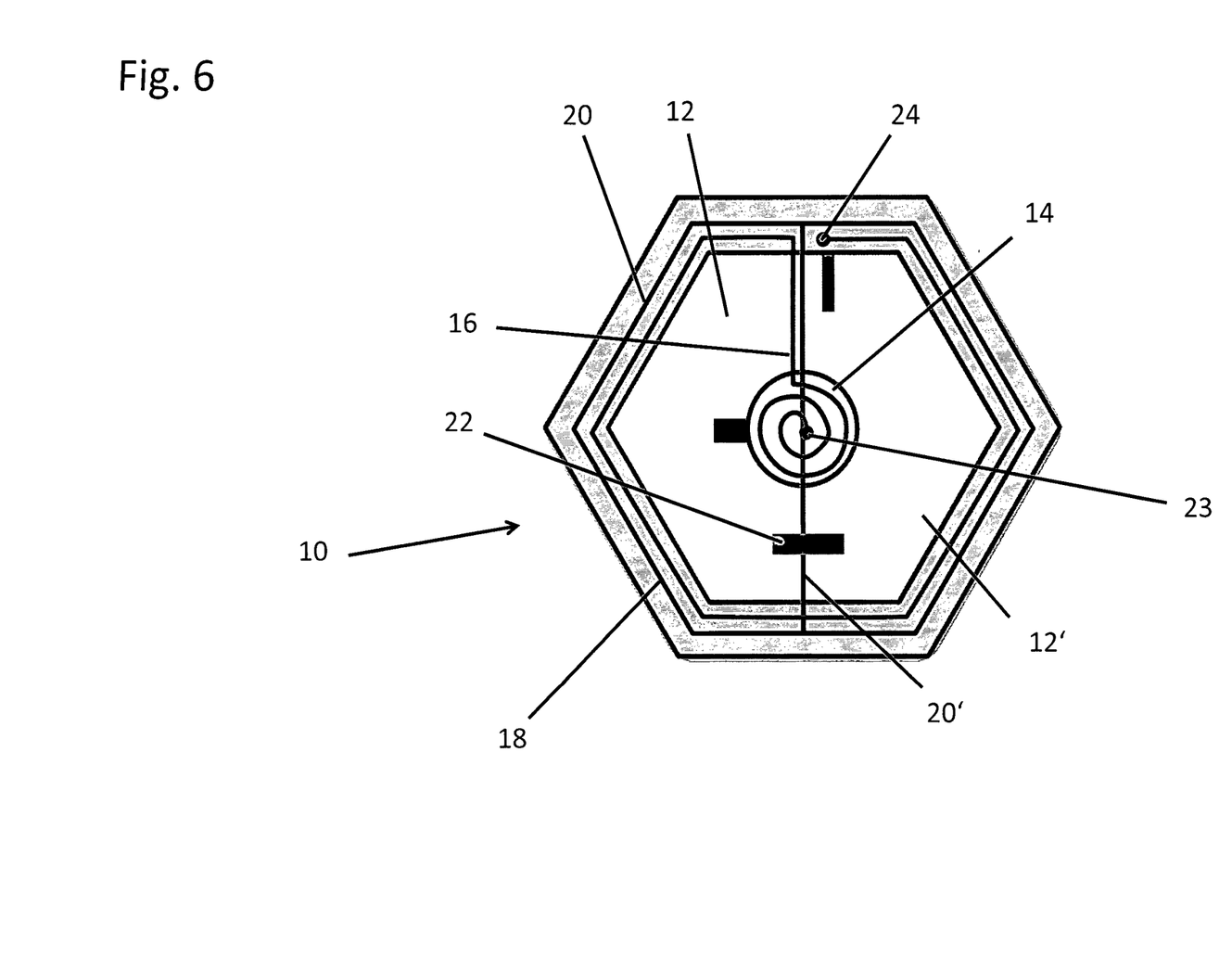
FIG. 6 is an example of a photosensitive pixel structure with a resistor according to an embodiment of the present invention.

FIG. 6 exemplifies a further embodiment of the present invention. Again, same reference signs refer to same or similar components and the repeated description thereof is omitted. Similar to the embodiment according to FIG. 1, the embodiment of FIG. 6 comprises two diodes, which are serially connected. The resistor 16, below the counter electrode 18, extends around almost the entire pixel structure 10, as already shown in FIG. 5. Further, the resistor 16 is formed in a spiral shape in an area covered by the stimulating electrode 14. In the embodiment shown in FIG. 6, the resistor 16 is looped twice and then extends in a straight fashion toward the counter electrode 18. By looping the resistor 16 below the stimulating electrode 14, the length of the resistor 16 may be increased, thus increasing the resistance of the resistor 16.

It will be understood that the exact shape of the wrapped resistor 16, in particular the way the resistor is wrapped below the stimulating electrode 14 may be in two loops, as shown in FIG. 6. Alternatively, the number of loops may be increased or reduced. Further, the contour, here the spiral-like looping, may also be a hexagonal shape, a half circle or half-spiral or any other shape suitable to increase the length of the resistor from the first electrical connection 23 to the circumference of the stimulating electrode 14 or, ultimately, to the second electrical connection 24 of the resistor 16 with the counter electrode 18.

The embodiment according to FIG. 6 represents one example for a small pixel structure 10, which, accordingly, requires a high resistance resistor. Thus, in the embodiment shown in FIG. 6, the resistor is provided in a way which allows maximized length while the diode area is affected as little as possible for the chosen structure.

The invention claimed is:

1. A photosensitive pixel structure for an implantable device configured to restore at least a portion of vision of a patient, the photosensitive structure comprising:
   a substrate;
   at least one photosensitive diode forming a photosensitive area, the at least one photosensitive diode being configured to receive light energy;
   a stimulating electrode configured to provide electrical stimulation to tissue of the patient to restore at least a portion of vision of the patient, the stimulating electrode generating an electrical pulse in response to the light energy received by the at least one photosensitive diode;
   a counter electrode; and
   a resistor, wherein the resistor electrically connects the stimulating electrode and the counter electrode,
   wherein the resistor is covered by the stimulating electrode and/or the counter electrode.

2. The photosensitive pixel structure according to claim 1, wherein the resistor is of an elongate type.

3. The photosensitive pixel structure according to claim 1, wherein the resistor is provided with a wrapped shape in an area covered by the stimulating electrode and/or the counter electrode.

4. The photosensitive pixel structure according to claim 1, wherein the substrate is a monocrystalline silicon substrate comprising at least a layer of $SiO_2$.

5. The photosensitive pixel structure according to claim 1, wherein the counter electrode and/or the resistor are arranged around at least a portion of an area occupied by the stimulating electrode and/or around an area occupied by the at least one diode.

6. The photosensitive pixel structure according to claim 1, wherein the resistor extends parallel to the counter electrode in an area of the pixel structure covered by the counter electrode.

7. The photosensitive pixel structure according to claim 1, wherein the resistor has an amorphous or a polycrystalline structure.

8. The photosensitive pixel structure according to claim 1, wherein the counter electrode is arranged around the stimulating electrode and/or around the at least one diode.

9. The photosensitive pixel structure according claim 1, wherein the photosensitive area has at least three sides, the resistor being disposed about a perimeter of the photosensitive area and extending adjacent to that at least three sides.

10. The photosensitive pixel structure according to claim 1, further comprising an isolating trench disposed adjacent to the photosensitive area, the resistor being disposed adjacent to the isolating trench and vertically overlapping the photosensitive area when viewed from a side of the photosensitive pixel structure.

11. A photosensitive pixel array for an implantable device configured to restore at least a portion of vision of a patient, the photosensitive pixel array, comprising:
    a plurality of photosensitive pixel structures arranged in an array, wherein each photosensitive pixel structure comprises:
    a substrate;
    at least one photosensitive diode forming a photosensitive area, the at least one photosensitive diode being configured to receive light energy;
    a stimulating electrode configured to provide electrical stimulation to tissue of the patient to restore at least a portion of vision of the patient, the stimulating electrode generating an electrical pulse in response to the light energy received by the at least one photosensitive diode;

a counter electrode; and a resistor, wherein the resistor electrically connects the stimulating electrode and the counter electrode, wherein the resistor is covered by the stimulating electrode and/or the resistor is at least partially covered by the counter electrode.

12. The photosensitive pixel array according to claim 11, wherein a central counter electrode is provided, wherein the central counter electrode is connected to each of a plurality of stimulating electrodes by a corresponding resistor.

13. An implant with a photosensitive pixel array according to claim 12.

14. The implant according to claim 13, wherein the implant is a subretinal implant.

15. The photosensitive pixel structure according to claim 11, wherein the counter electrode and/or the resistor are arranged around at least a portion of an area occupied by the stimulating electrode and/or around an area occupied by the at least one diode.

16. The photosensitive pixel structure according to claim 11, wherein the resistor extends parallel to the counter electrode in an area of the pixel structure covered by the counter electrode.

17. The photosensitive pixel structure according to claim 11, wherein the resistor has an amorphous or a polycrystalline structure.

18. The photosensitive pixel structure according to claim 11, wherein the counter electrode is arranged around the stimulating electrode and/or around the at least one diode.

19. The photosensitive pixel array according claim 11, wherein the photosensitive area has at least three sides, the resistor being disposed about a perimeter of the photosensitive area and extending adjacent to that at least three sides.

20. The photosensitive pixel structure according to claim 11, further comprising an isolating trench disposed adjacent to the photosensitive area, the resistor being disposed adjacent to the isolating trench and vertically overlapping the photosensitive area when viewed from a side of the photosensitive pixel structure.

21. A method to provide a pixel structure for an implantable device configured to restore at least a portion of vision of a patient, the photosensitive pixel array the pixel structure includes a substrate, at least one photosensitive diode forming a photosensitive area, the at least one photosensitive diode being configured to receive light energy, a stimulating electrode configured to provide electrical stimulation to tissue of the patient, a counter electrode, and a resistor, wherein the resistor electrically connects the stimulating electrode and the counter electrode and wherein the resistor is at least partially covered by the stimulating electrode and/or the resistor is at least partially covered by the counter electrode, the method comprising:

providing the substrate;

providing at least one photosensitive diode area on the substrate to form a photosensitive area, providing, on the substrate, a resistor in an area that is not occupied by the at least one photosensitive diode, providing the stimulating electrode configured to provide electrical stimulation to tissue of the patient and/or the counter electrode on the substrate to restore at least a portion of vision of the patient, the stimulating electrode generating an electrical pulse in response to the light energy received by the at least one photosensitive diode, wherein the stimulating electrode and/or the counter electrode cover the resistor.

22. The method according to claim 21, wherein the resistor is provided as a straight, elongate structure and/or at least partially as a wrapped structure.

23. The method according to claim 21, wherein the resistor is provided by atom doping of the substrate.

24. The method according to claim 21, wherein the resistor is provided by atom doping of a thin strip of a material selected from a group that includes amorphous silicon and polysilicon.

25. The method according to claim 21, wherein the resistor is provided by forming a first shunt resistor of a first material and a second shunt resistor of a second material different from the first material and connecting the first shunt resistor and the second shunt resistor in series.

26. The method according to claim 21, wherein the resistor is provided by forming a first shunt resistor of a first material and a second shunt resistor of a second material different from the first material and connecting the first shunt resistor and the second shunt resistor in parallel.

27. The method according to claim 24, wherein the first material is a metal that forms a metallization layer that interconnects the photosensitive diodes to each other and which interconnects the at least one photosensitive diode to the stimulating electrode and the counter electrode.

* * * * *